US00PP37490P2

(12) United States Plant Patent
Grazzini

(10) Patent No.: US PP37,490 P2
(45) Date of Patent: Jun. 23, 2026

(54) ***COLEUS* PLANT NAMED 'G22026'**

(50) Latin Name: *Coleus scutellarioides*
Varietal Denomination: G22026

(71) Applicant: Garden Genetics llc, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 19/354,494

(22) Filed: Oct. 9, 2025

(51) Int. Cl.
*A01H 5/02* (2018.01)
*A01H 6/50* (2018.01)

(52) U.S. Cl.
USPC ..... Plt./469

(58) Field of Classification Search
USPC ..... Plt./263.1, 469
See application file for complete search history.

(56) References Cited

U.S. PATENT DOCUMENTS

PP30,621 P2 * 6/2019 Clark ..... A01H 5/12
Plt./373

* cited by examiner

*Primary Examiner* — Karen M Redden

(57) ABSTRACT

A new and distinct cultivar of *Coleus* plant named 'G22026' is disclosed, characterized by a compact, densely branched plant habit forming an ovate-globose shape. Foliage is bright golden green with a dark red center. Floral initiation begins in mid to late October, at 41N latitude, under natural daylength. Foliage is strongly resistant to *Coleus* downy mildew (CDM), caused by *Peronospora choii*. The new cultivar is a *Coleus*, typically produced as an outdoor ornamental plant or for garden or container uses.

1 Drawing Sheet

Latin name of the genus and species: *Coleus scutellarioides.*

Variety denomination: 'G22026'.

BACKGROUND OF THE INVENTION

The new cultivar is the product of a planned breeding program conducted by the inventor. New variety 'G22026' is a seedling selected from seed harvested as an isolated mass population in October 2021 and sown in January 2022. The isolated mass population consisted of internally developed *Coleus* varieties and breeding lines, and was grown in containers in an isolated location at a research nursery in Bellefonte, PA. The new variety was found and selected by the inventor in March of 2022 at the same research greenhouse in Bellefonte, Pennsylvania.

Asexual reproduction of the new cultivar 'G22026' by terminal vegetative cuttings was performed at the same nursery in Bellefonte, Pennsylvania in March of 2022. Subsequent asexual reproduction, both by terminal cuttings and tissue culture has shown that the unique features of this cultivar are stable and reproduced true to type through successive generations.

SUMMARY OF THE INVENTION

The cultivar 'G22026' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G22026'.

These characteristics in combination distinguish 'G22026' as a new and distinct *Coleus* cultivar:

1. Compact, uniform, densely branched habit.
2. Plant is typically globular to ovate in shape, 30 to 32 in (76 to 81 cm) in both height and 24 to 28 inches (61 to 71 cm) in width.
3. Plants are densely-branched and self-supporting-resisting lodging.
4. Foliage color is bright green-gold with a dark red center.
5. Foliage is strongly resistant to *Coleus* downy mildew (CDM), caused by *Peronospora choii*. No symptoms of CDM have been observed on plants of 'G22026' since its selection in 2022 in greenhouse, outdoor container, or outdoor in-ground trials. In those same trials, CDM-susceptible *Coleus* varieties were observed to suffer foliage losses due to CDM infection at rates from 25% to 100%.
6. Floral initiation begins in mid to late October at 41N latitude, under natural daylengths.
7. Foliage is strongly sun-tolerant in full sun at 41N latitude for the entire gardening season. To reliably demonstrate sun-tolerance, plants need to be routinely fertilized and watered.

PARENT COMPARISON

Parental varieties cannot be identified.

COMMERCIAL COMPARISON

'G22026' can be compared to the commercially known variety *Coleus* 'Wizard Golden', unpatented. These plants are similar in most horticultural characteristics. However, plants of the new cultivar 'G22026' differ in the following ways:

1. 'G22026' is less vigorous and more compact than 'Wizard Golden'.
2. Foliage of 'G22026' is larger in both length and width than foliage of 'Wizard Golden'.
3. 'G22026' has a distinct dark red-violet splash along the mid-rib of the leaf, whereas 'Wizard Golden' has no such splash.
4. The new cultivar blooms about 8 to 12 weeks later than this comparator.
5. 'G22026' exhibits much stronger resistance/tolerance to *Coleus* downy mildew (CDM) caused by *Peronospora choii* than comparison variety 'Wizard Golden'.

'G22026' can also be compared to the commercially known variety *Coleus* 'UF16-27-1', U.S. Plant Pat. No. 30,621. These cultivars are similar in most horticultural characteristics. However, plants of the new cultivar 'G22026' differ in the following:

1. 'G22026' is more vigorous and less compact than 'UF16-27-1'. Mature size of the new cultivar is 30 to 32 inches (76 to 81 cm) tall and 24 to 28" (61 to 71 cm) versus 14 inches (35 cm) tall by 24 inches (60 cm) wide for this comparator.
2. Foliage of 'G22026' is larger in both length and width than foliage of 'UF16-27-1'.
3. 'G22026' has a distinct dark red-violet splash along the mid-rib of the leaf, whereas 'UF16-27-1' has no such splash.
4. The new cultivar blooms about 2 to 4 weeks later than this comparator.
5. 'G22026' exhibits much stronger resistance/tolerance to *Coleus* downy mildew (CDM) caused by *Peronospora choii* than comparison variety 'UF16-27-1'.

BRIEF DESCRIPTION OF THE PHOTOGRAPH

The accompanying photograph illustrates a close-up view of the mature foliage on a plant of about 5 months old grown in Columbus, OH. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart 2015, except where general terms of ordinary dictionary significance are used. The following observations and measurements describe 'G22026' plants grown outdoors during Summer in Camarillo, California. The growing temperature ranged from about 7° C. to 28° C. during the day and from about 5° C. to 18° C. during the night. General light conditions are bright, normal sunlight. Measurements and numerical values represent averages of typical plant types. Plants are approximately 4 months old from a rooted cutting. No chemical or photoperiodic treatments were given.

Botanical classification: *Coleus scutellarioides* 'G22026'.

PROPAGATION

Root description: Fine, well-branched, fibrous, becoming slightly woody with age. Colored near Greyed-Yellow-161D and White 155A.

PLANT

Growth habit: Tender herbaceous perennial. Upright.

Height: Approximately 45 cm.

Plant spread: Approximately 35 cm.

Branching characteristics: Basal and lateral branching.

Length of branches: Approximately 10 to 25 cm.

Diameter branches: Approximately 6 to 8 mm.

Quantity of branches: Approximately 4 to 6 basal branches, each basal branch with 3 to 5 lateral branches.

Texture of lateral branches: Glabrous and ridged.

Color of lateral branches:

*Upper surface*.—Greyed-Purple N186B flushed 186C. Very infrequent speckles Yellow-Green 144C.

*Lower surface*.—Yellow-Green 144C. Infrequently speckled 186C.

Aspect: Approximately 20° to 45° angle from center of plant.

Strength of lateral branches: Moderate. Not easily broken, no brittleness.

Internode length: Average range 3 to 5 cm.

Age of plant described: Approximately 4 months old.

FOLIAGE

Arrangement: Opposite.

Average Length: Average range 11 to 17 cm.

Average Width: Average range 7 to 11 cm.

Shape of blade: Ovate.

Apex: Acute.

Base: Rounded.

Attachment: Petiolate.

Margin: Crenate.

Texture of top surface: Very minute, slightly rough pubescent.

Texture of bottom surface: Non-pubescent with protruding veins.

Foliage color:

*Young foliage upper side*.—Yellow-Green N144C. Large central blotch covering 50% to 70% of the blade, shaped like the leaf blade colored 187B. Some speckling outside of the blotch also 187B.

*Young foliage under side*.—Yellow-Green N144D. Faint central blotch, covering about 50% of the blade, shaped like the leaf blade colored N187C. Some speckling outside of the blotch also N187C.

*Mature foliage upper side*.—Yellow-Green N144C. Large central blotch covering 60% to 75% of the blade, shaped like the leaf blade colored 187A. 187A bleeds out from central blotch along veins nearly to the margin. Some small speckling outside of the blotch also 187A. Along mid-vein bleeding of strong Red-Purple 61B. Small lines of Yellow-Green 145C in the 61B.

*Mature foliage under side*.—Yellow-Green 145A. Faint central blotch, covering about 50% to 70% of the blade, shaped like the leaf blade colored very faint N187A. Along mid-vein some bleeding of 62D.

Venation:

*Type*.—Pinnate. Venation color upper side: Near RHS Red-Purple 61A in Red-Purple center. From base to center Yellow-Green 145D. Upper section Greyed-Purple N186C. Venation color under side: Lower half near Yellow-Green 145D, lightly flushed N186D. Flushing stronger near petiole attachment. Upper half Yellow-Green 145B.

Petiole:

*Length*.—Average range 2.5 to 4.5.

*Diameter*.—Average 5.5 mm.

*Color*.—Upper: Yellow-Green 145D flushed 61B along edges. Lower: Yellow-Green 145D flushed lightly 61A and N186D.
*Texture*.—Glabrous.

INFLORESCENCE

Natural flowering season: Floral initiation may begin in mid to late September at 41N latitude. Flowering may not be observed every year.
Inflorescence type and habit: Terminal raceme.
Individual flowers: Zygomorphic flowers facing outward.
Longevity of individual flowers: About 3 weeks.
Fragrance: None
Inflorescence size:
*Length*.—7 to 12 cm.
*Width*.—4 cm.
Quantity of flowers per inflorescence: About 12 to 36.
Corolla:
*Shape*.—Bilabiate, tubular.
*Aspect*.—Outward.
*Persistence*.—Self-cleaning.
*Size*.—About 15 mm long and 5 mm wide.
Petals:
*Upper lip*.—Width: 7 mm. Length: 5 mm. Apex: Obtuse, rounded, composed of 2 fused lobes. Base: Fused to central petal. Margin: Entire. Texture: Front: Glabrous. Back: Glabrous. Color: Upper surface: RHS Violet-Blue 91D. Lower surface: RHS Violet-Blue 91D.
*Lower lip*.—Width: 5 mm (folded). Length: 1 cm. Apex: Obtuse, rounded. Base: Fused. Margin: Entire. Texture: Front: Glabrous. Back: Glabrous. Color: Upper surface: RHS Violet-Blue N89C. Base 91D. Lower surface: RHS Violet-Blue 90D. Base White N155A.
*Tube*.—Diameter: 3 mm. Length: 5 mm. Color: Inner: RHS Violet-Blue 91D. Outer: RHS Violet-Blue 91D. Texture: Glabrous.
Bud:
*Shape*.—Ovate.
*Color*.—Base Violet-Blue 91D, apex 90A.
*Size*.—5 mm in height and 4 mm in diameter.
*Texture*.—Glabrous.
Calyx: Bell-shaped, composed of 5 sepals fused at base.
Sepals:
*Shape*.—Elliptic.
*Apex*.—Acute.
*Base*.—Fused.
*Margin*.—Entire.
*Length*.—5 mm.
*Width*.—3 mm.
*Texture*.—Glabrous, upper and lower surfaces.
*Color*.—Upper surface: RHS Yellow-Green 145A. Lower surface: RHS Yellow-Green 145B.
Peduncle:
*Shape*.—Quadrate with prominent longitudinal veins.
*Length*.—2 to 5 cm.
*Diameter*.—4 mm.
*Strength*.—Medium.
*Texture*.—Glabrous.
*Color*.—RHS Yellow-Green N144D.
Pedicel:
*Orientation*.—45° to 90° from peduncle.
*Texture*.—Glabrous.
*Length*.—5 to 7 mm.
*Diameter*.—2 mm.
*Color*.—RHS Yellow-Green 144B.
*Strength*.—Medium.

REPRODUCTIVE ORGANS

Androecium:
*Number of stamens*.—4 per flower, non-protruding.
*Filament*.—Unfused segment about 4 mm, colored near White N155C.
*Pollen*.—Not observed.
Gynoecium:
*Pistil number*.—1 per flower.
*Pistil length*.—15 mm.
*Style length*.—8 mm.
*Style color*.—RHS White N155C.
*Stigma shape*.—Two-parted.
*Stigma color*.—White N155C.
*Ovary color*.—RHS Yellow-Green N144D.

OTHER CHARACTERISTICS

Disease resistance: Foliage is strongly resistant to *Coleus* downy mildew (CDM), caused by *Peronospora choii*. No symptoms of CDM have been observed on new variety 'G21015' since its selection in 2021 in greenhouse, outdoor container, or outdoor in-ground trials. In those same trials, CDM-susceptible *Coleus* varieties were observed to suffer foliage losses due to CDM infection at rates from 25% to 100%. Neither resistance nor susceptibility to other diseases or to pests normal to *Coleus* have been observed in this cultivar.
Drought tolerance and temperature tolerance: No tolerance for drought. Tender perennial, USDA zones 10-11. Summer annual in colder zones.
Fruit/seed production: Not observed to date.

What is claimed is:

1. A new and distinct cultivar of *Coleus* plant named 'G22026' as herein illustrated and described.

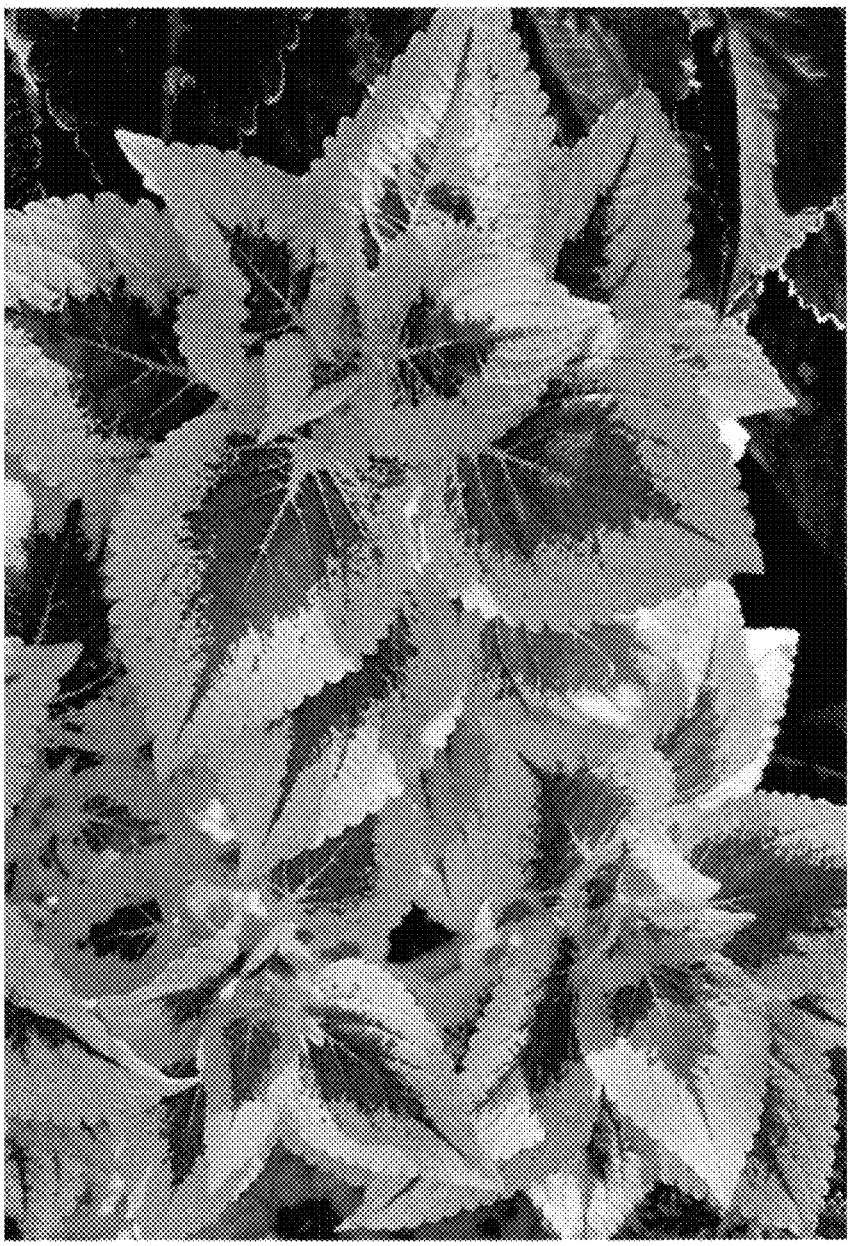

* * * * *